(12) United States Patent
Osypka

(10) Patent No.: US 9,844,644 B2
(45) Date of Patent: Dec. 19, 2017

(54) INTRAVASCULAR SHEATH WITH MAPPING CAPABILITIES TO DELIVER THERAPEUTIC DEVICES TO A TARGETED LOCATION WITHIN A BLOOD VESSEL

(71) Applicant: Oscor Inc., Palm Harbor, FL (US)

(72) Inventor: Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 358 days.

(21) Appl. No.: 14/632,229

(22) Filed: Feb. 26, 2015

(65) Prior Publication Data

US 2015/0250982 A1 Sep. 10, 2015

Related U.S. Application Data

(60) Provisional application No. 61/948,288, filed on Mar. 5, 2014.

(51) Int. Cl.
*A61B 19/00* (2006.01)
*A61M 25/01* (2006.01)
(Continued)

(52) U.S. Cl.
CPC ......... *A61M 25/0105* (2013.01); *A61B 18/02* (2013.01); *A61B 18/1492* (2013.01);
(Continued)

(58) Field of Classification Search
CPC ........... A61M 2025/0166; A61N 1/372; A61N 1/37205; A61B 18/1492
See application file for complete search history.

(56) References Cited

U.S. PATENT DOCUMENTS 5,833,688 A * 11/1998 Sieben ............... A61B 18/1492
606/15
6,226,554 B1 * 5/2001 Tu ....................... A61B 18/1492
606/41
(Continued)

OTHER PUBLICATIONS

Office Action for European Patent Appliction No. 15157637.8, dated Jul. 19, 2016.
(Continued)

*Primary Examiner* — Ashley Fishback
(74) *Attorney, Agent, or Firm* — Locke Lord LLP; Scott D. Wofsy

(57) ABSTRACT

A surgical apparatus is disclosed for delivering a therapeutic device to a desired location within the vasculature of a patient, which includes an elongated tubular body defining a longitudinal axis and having opposed proximal and distal end portions, the tubular body including an outer wall surrounding an interior lumen, wherein an elongated target opening is formed through the outer wall of the tubular body within the distal end portion thereof in communication with the interior lumen. At least one distal sensing electrode is provided on the tubular body adjacent a distal side of the target opening, and at least one proximal sensing electrode is provided on the tubular body adjacent a proximal side of the target opening, wherein the sensing electrodes allow placement of the target opening within the vasculature of a patient for the delivery of a therapeutic device to a desired location.

16 Claims, 2 Drawing Sheets

(51) Int. Cl.
A61B 18/14 (2006.01)
A61B 18/02 (2006.01)
*A61B 18/00* (2006.01)

(52) U.S. Cl.
CPC ............... *A61B 2018/0022* (2013.01); *A61B 2018/00196* (2013.01); *A61B 2018/00404* (2013.01); *A61B 2018/00434* (2013.01); *A61B 2018/00511* (2013.01); *A61B 2018/00577* (2013.01); *A61B 2018/00839* (2013.01); *A61M 2025/0166* (2013.01)

(56) References Cited

U.S. PATENT DOCUMENTS

| | | | |
|---|---|---|---|
| 2005/0015048 A1* | 1/2005 | Chiu | A61M 25/10 604/101.04 |
| 2005/0267459 A1 | 12/2005 | Belhe et al. | |
| 2006/0085041 A1 | 4/2006 | Hastings et al. | |
| 2009/0209950 A1* | 8/2009 | Starksen | A61B 5/0215 606/21 |
| 2013/0103026 A1 | 4/2013 | Kleshinski et al. | |
| 2013/0223702 A1 | 8/2013 | Holsing et al. | |
| 2013/0274730 A1* | 10/2013 | Anderson | A61B 18/18 606/33 |
| 2013/0324987 A1 | 12/2013 | Leung et al. | |

OTHER PUBLICATIONS

Extended Search Report dated Jul. 29, 2015 in connection with corresponding EP Patent Application No. 15157637.8.

\* cited by examiner

INTRAVASCULAR SHEATH WITH MAPPING CAPABILITIES TO DELIVER THERAPEUTIC DEVICES TO A TARGETED LOCATION WITHIN A BLOOD VESSEL

CROSS-REFERENCE TO RELATED APPLICATION

This application claims the benefit of and priority to U.S. Provisional Patent Application No. 61/948,288 filed Mar. 5, 2014, which is incorporated herein by reference.

BACKGROUND OF THE INVENTION

1. Field of the Invention

The subject invention is directed to intravascular surgery, and more particularly, to a system and apparatus with mapping capabilities to deliver a therapeutic device to a targeted location within the blood vessel of a patient.

2. Description of Related Art

Currently many minimal invasive intravascular medical procedures are performed blind or without direct vision by the physician. As a result, the physician performs the procedure without having a detailed knowledge of the exact location in which to perform a particular intravascular therapeutic treatment. An example of such a procedure is renal denervation.

In renal denervation, the complete renal artery is ablated with several ablation electrodes in parallel to achieve the blockage of the nervous system around the renal artery. Typically, during renal denervation, the site of the procedure within the renal artery is located through X-ray and/or ultrasound. Thus, there is no direct knowledge of the exact location of the critical nerve, and many times this can result in immense pain to the patient.

It would therefore be advantageous to have an intravascular delivery system that would allow the precise mapping of critical nerve signals within a blood vessel, so as to enable a physician to locate the best and exact location or site to perform a particular therapeutic treatment, which then enables the introduction of a therapeutic device, such as an ablation catheter, or the delivery of a therapeutic drug to that site or location. The localized treatment would be more effective, allowing less energy (and or drug) to be used to be effective, and would result in less pain and side effects for the patient.

SUMMARY OF THE INVENTION

The subject invention is directed to a new and useful surgical apparatus and system for delivering a therapeutic device to a desired location within the vasculature of a patient in connection with the performance of a procedure such as for example, renal denervation or a similar procedure in another blood vessel.

The apparatus includes an elongated tubular body or sheath defining a longitudinal axis and having opposed proximal and distal end portions, the tubular body including an outer wall surrounding an interior lumen, wherein an elongated target opening is formed through the outer wall of the tubular body within the distal end portion thereof in communication with the interior lumen.

At least one distal sensing electrode is provided on the tubular body adjacent a distal side of the target opening, and at least one proximal sensing electrode provided on the tubular body adjacent a proximal side of the target opening, wherein the distal and proximal sensing electrodes allow placement of the target opening within the vasculature of a patient for the delivery of a therapeutic device to a desired location. The target opening facilitates sideway exit of a therapeutic device introduced through the lumen.

Preferably, the distal and proximal sensing electrodes are electrically connected through one or more conductor wires extending through the wall of the body to the proximal hub for connection to a meter that displays and/or records sensing wave forms corresponding to nerve signals detected by the sensing electrodes.

Preferably, the body has a tapered and closed distal end portion, and the body has a hub at the proximal end portion thereof defining an opening to the interior lumen. The lumen can have a luer lock fitting and/or hemostatic valve at the proximal hub. The proximal hub may include a side port having a three-way stop cock.

The system for delivering a therapeutic device to a desired location within the vasculature of a patient includes a surgical apparatus having an elongated tubular body defining a longitudinal axis and having opposed proximal and distal end portions. The tubular body includes an outer wall surrounding an interior lumen. A target opening is formed through the outer wall of the tubular body within the distal end portion thereof in communication with the interior lumen. The surgical apparatus further includes at least one distal sensing electrode provided on the tubular body adjacent a distal side of the target opening and at least one proximal sensing electrode provided on the tubular body adjacent a proximal side of the target opening.

A therapeutic device is introduced through the proximal hub into the interior lumen. A metering system is electronically coupled to the at least one distal sensing electrode and the at least one proximal sensing electrode for determining the exact positioning of the target opening within the vasculature of a patient.

These and other features of the delivery system of the subject invention and the manner in which it is manufactured and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the subject invention appertains will readily understand how to make and use the subject invention without undue experimentation, preferred embodiments thereof will be described in detail herein below with reference to certain figures, wherein.

DETAILED DESCRIPTION OF PREFERRED EMBODIMENTS

Figure 1:
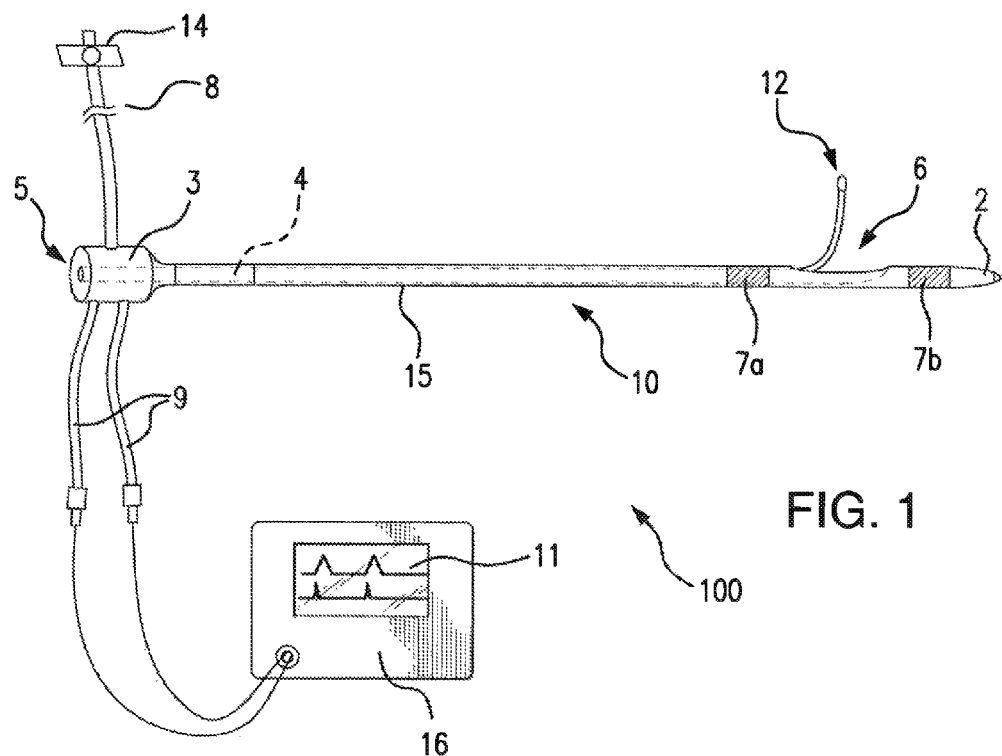
FIG. 1 is a side elevational view of the surgical apparatus of the subject invention connected to a meter.

Referring now to the drawings wherein like reference numerals identify similar structural elements or features of the invention, there is illustrated in FIG. 1 a surgical system constructed in accordance with the subject disclosure and designated generally by reference numeral 100. The surgical system 100 includes an elongated tubular sheath or catheter body 10 having an outer wall 15. The catheter body or sheath 10 has a tapered distal end portion 2 that is closed and a proximal end portion defining a hub 3.

With continuing reference to FIG. 1, an interior lumen 4 extends through the elongated sheath or catheter body 10 from the proximal hub 3 to facilitate the delivery of a therapeutic device such as an ablation catheter, cyro-balloon catheter or a needle-type drug delivery system into the vasculature of a patient. The interior lumen 4 has a leur lock fitting and/or a hemostatic valve 5 within the entrance to the proximal hub 3 to allow for the insertion of contrast media and/or saline solution to enable catheter aspiration through an optional side port 8 having a three-way stop cock valve 14 or the like.

The distal end portion 2 of the catheter body has an elongated target opening 6 formed through the outer wall 15 of the body that communicates with the interior lumen 4. The target opening 6 is formed to one side of the catheter body 10, allowing for the sideways exit of a therapeutic catheter 12, as shown in FIG. 1. On both ends of the target opening 6 there is at least one sensing electrode 7a, 7b, allowing the mapping and sensing of electrical signals transmitted by the nervous system and nerve bundles of the human nerve system.

Figure 2:
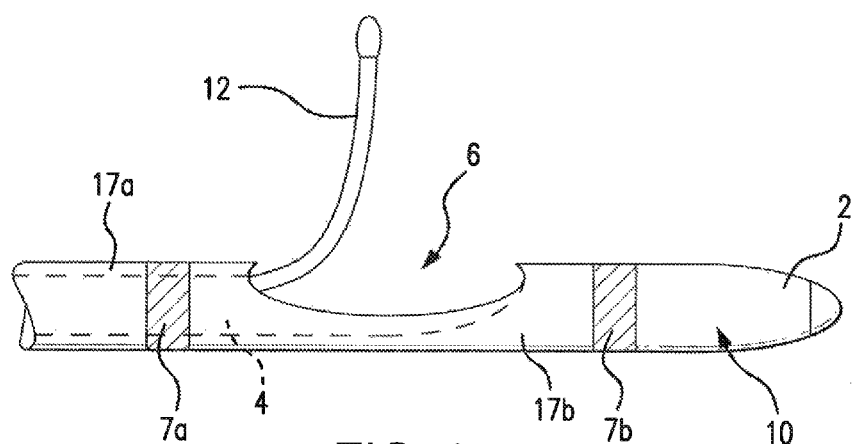
FIG. 2 is an enlarged localized view of the distal end portion of the device shown in FIG. 1.

For example, as shown in FIG. 2, a first annular sensing electrode 7a is provided on the catheter body 10 adjacent a proximal side of the target opening 6 and a second annular sensing electrode 7b is provided on the catheter body 10 adjacent a distal side of the target opening 6. It is envisioned that two or more sensing electrodes may be provided on the distal and proximal sides of the target opening 6 for enhanced targeting.

These distal and proximal sensing electrodes 7a, 7b are electrically connected through one or more conductor wires 17a, 17b that extend through the wall 15 of the sheath body 10 to the proximal hub 3. At the proximal hub 3, the conductor wires 17a, 17b can be connected via connectors 9 to a resistance/impedance meter 16. The meter 16 displays and/or records sensing wave forms on a display 11 that correspond to nerve signals detected by the sensing electrodes. This mapping and sensing of electrical nerve signals allows the exact positioning of the catheter target opening 6, and when located and positioned correctly, the therapeutic device 12 can be delivered, or a therapeutic treatment such as RF ablation or cyro ablation performed at the desired target location.

Figure 3:
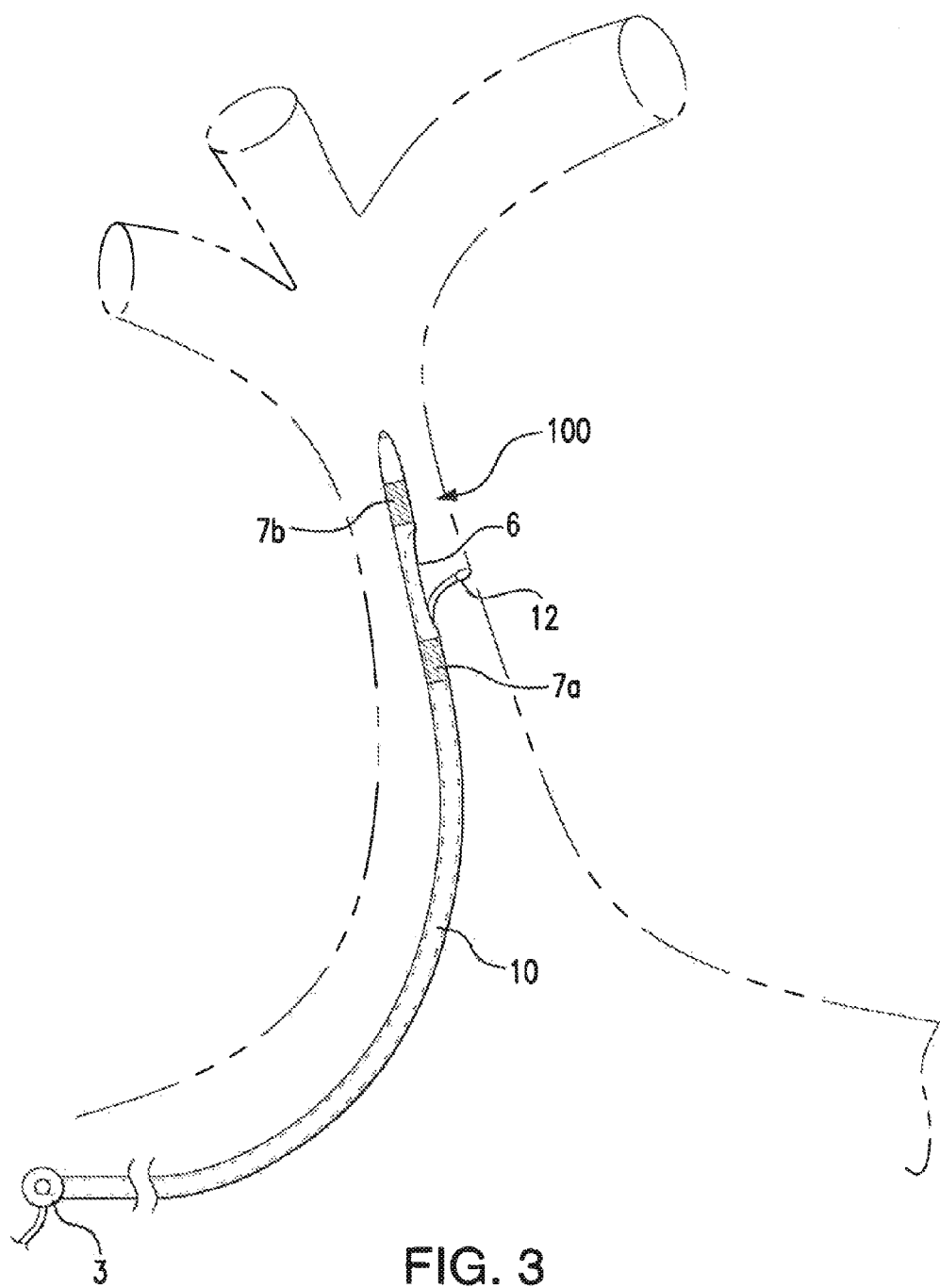
FIG. 3 is an illustration of the surgical apparatus of the subject invention while in use during an intravascular procedure.

Referring to FIG. 3, the mapping and sensing of electrical nerve signals allows for the exact positioning of the catheter target opening 6 of body 10 within the vasculature of a patient. When the target opening 6 is located and positioned correctly, a therapeutic device 12 can be readily delivered from the interior lumen 4 and a therapeutic treatment such as RF ablation and/or cryo-ablation can be performed at the desired target location.

The introducer system 100 of the subject invention could be delivered either directly into the vein or artery as shown in FIG. 3, or it could be delivered and introduced via another introducer or guiding sheath system, such as a steerable guiding sheath. An application for this system could be, for example, the renal artery, to be used for the exact mapping of the nerve activities, so a therapeutic application such as renal denervation could be applied at the exact localized area.

A method of using the introducer system 100 includes inserting the distal end of the sheath 10 through a vein or artery, for example, requiring a therapeutic device. Once the sheath is inserted, the proximal and distal sensing electrodes 7a, 7b can be activated. Nerve signals detected by the sensing electrodes 7a, 7b are displayed on the meter to determine the best and exact location for delivering the therapeutic device 12. The therapeutic device 12 is then inserted into the lumen 14 through the proximal hub 3 and advanced through the lumen to the target opening. Through the target opening, the therapeutic device 12 exits the lumen and sheath to reach the determined location.

While the subject invention has been shown and described with reference to preferred embodiments, those skilled in the art will readily appreciate that various changes and/or modifications may be made thereto without departing from the spirit and scope of the subject invention as defined by the appended claims.

What is claimed is:

1. A surgical apparatus for delivering a therapeutic device to a desired location within the vasculature of a patient, comprising:
   a) an elongated tubular body defining a longitudinal axis and having opposed proximal and distal end portions, the tubular body including an outer wall surrounding an interior lumen, wherein an elongated target opening is formed through the outer wall of the tubular body within the distal end portion thereof in communication with the interior lumen;
   b) a therapeutic device extending through the interior lumen and configured to be advanced through the target opening;
   c) at least one distal sensing electrode provided on the tubular body adjacent a distal side of the target opening; and
   d) at least one proximal sensing electrode provided on the tubular body adjacent a proximal side of the target opening, wherein the distal and proximal sensing electrodes allow placement of the target opening within the vasculature of a patient for the advancement of the therapeutic device from the interior lumen through the target opening to a desired location.

2. The surgical apparatus as recited in claim 1, wherein the body has a tapered and closed distal end portion.

3. The surgical apparatus as recited in claim 1, wherein the body has a hub at the proximal end portion thereof defining an opening to the interior lumen.

4. The surgical apparatus as recited in claim 3, wherein the lumen has a leur lock fitting and/or hemostatic valve at the proximal hub.

5. The surgical apparatus as recited in claim 3, wherein the proximal hub includes a side port having a three-way stop cock.

6. The surgical apparatus as recited in claim 1, wherein the distal and proximal sensing electrodes are electrically connected through one or more conductor wires extending through the wall of the body to a proximal hub for connection to a meter that displays and/or records sensing wave forms corresponding to nerve signals detected by the sensing electrodes.

7. The surgical apparatus as recited in claim 1, wherein the target opening facilitates sideway exit of a therapeutic device introduced through the lumen.

8. A system for delivering a therapeutic device to a desired location within a vasculature of a patient, comprising:
   a) a surgical apparatus including:
      i) an elongated tubular body defining a longitudinal axis and having opposed proximal and distal end portions, the tubular body including an outer wall surrounding an interior lumen, wherein a target opening is formed through the outer wall of the tubular body within the distal end portion thereof in communication with the interior lumen;

ii) at least one distal sensing electrode provided on the tubular body adjacent a distal side of the target opening; and iii) at least one proximal sensing electrode provided on the tubular body adjacent a proximal side of the target opening;

b) a therapeutic device introduced through a proximal hub into the interior lumen and configured to be advanced through the target opening; and c) a metering system electronically coupled to the at least one distal sensing electrode and the at least one proximal sensing electrode for determining the exact positioning of the target opening within the vasculature of a patient.

9. The system as recited in claim 8, wherein the distal and proximal sensing electrodes are electrically connected through one or more conductor wires extending through the wall of the body to the proximal hub for connection to a meter that displays and/or records sensing wave forms corresponding to nerve signals detected by the sensing electrodes.

10. The system as recited in claim 8, wherein the target opening facilitates sideway exit of a therapeutic device introduced through the lumen.

11. The system as recited in claim 8, wherein the body has a tapered and closed distal end portion.

12. The system as recited in claim 8, wherein the lumen has a leur lock fitting and/or hemostatic valve at the proximal hub.

13. The system as recited in claim 8, wherein the proximal hub includes a side port having a three-way stop cock.

14. A method for delivering a therapeutic device to a desired location within a vasculature of a patient, the steps comprising:

a) providing a surgical apparatus including:

i) an elongated tubular body defining a longitudinal axis and having opposed proximal and distal end portions, the tubular body including an outer wall surrounding an interior lumen, wherein a target opening is formed through the outer wall of the tubular body within the distal end portion thereof in communication with the interior lumen;

ii) at least one distal sensing electrode provided on the tubular body adjacent a distal side of the target opening; and iii) at least one proximal sensing electrode provided on the tubular body adjacent a proximal side of the target opening;

b) facilitating insertion of the distal end portion of the surgical apparatus within the vasculature of the patient;

c) accepting a therapeutic device through a proximal hub into the interior lumen;

d) sensing nerve signals using the at least one distal sensing electrode and the at least one proximal sensing electrode to determine the best location for placement of the therapeutic device; and e) facilitating placement of the therapeutic device at the best location by advancing the therapeutic device from the interior lumen through the target opening.

15. The method of claim 14, wherein the step of sensing includes displaying the nerve signals through a metering system electronically coupled to the at least one distal sensing electrode and the at least one proximal sensing electrode for determining the exact positioning of the target opening within the vasculature of a patient.

16. The method of claim 14, wherein the step of facilitating placement of the therapeutic device includes providing a sideway exit from the interior lumen.

* * * * *